(12) United States Patent
Boese et al.

(10) Patent No.: US 7,657,069 B2
(45) Date of Patent: Feb. 2, 2010

(54) METHOD FOR ENDOLUMINAL IMAGING WITH MOVEMENT CORRECTION

(75) Inventors: Jan Boese, Eckental (DE); Martin Kleen, Furth (DE); Marcus Pfister, Erlangen (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 707 days.

(21) Appl. No.: 11/076,537

(22) Filed: Mar. 8, 2005

(65) Prior Publication Data

US 2005/0197559 A1    Sep. 8, 2005

(30) Foreign Application Priority Data

Mar. 8, 2004   (DE)   .................. 10 2004 011 156

(51) Int. Cl.
*G06K 9/00* (2006.01)

(52) U.S. Cl. ....................................... 382/128

(58) Field of Classification Search ................ 382/100, 382/128–134; 600/407, 424, 428; 128/920–930; 250/455–465; 356/39–49
See application file for complete search history.

(56) References Cited

U.S. PATENT DOCUMENTS

| | | | |
|---|---|---|---|
| 5,738,096 A * | 4/1998 | Ben-Haim | .................. 600/407 |
| 5,830,145 A | 11/1998 | Tenhoff | |
| 5,924,989 A | 7/1999 | Polz | |
| 6,095,976 A * | 8/2000 | Nachtomy et al. | .......... 600/443 |
| 6,248,074 B1 | 6/2001 | Ohno et al. | |
| 6,317,621 B1 | 11/2001 | Graumann et al. | |
| 6,447,450 B1 | 9/2002 | Olstad | |
| 2002/0049375 A1 | 4/2002 | Strommer et al. | |
| 2002/0077546 A1 | 6/2002 | Aldefeld et al. | |
| 2003/0123606 A1 | 7/2003 | Mollus et al. | |
| 2004/0092815 A1 * | 5/2004 | Schweikard et al. | ........ 600/425 |
| 2004/0120557 A1 * | 6/2004 | Sabol et al. | ................. 382/128 |

FOREIGN PATENT DOCUMENTS

| | | |
|---|---|---|
| EP | 1 189 175 A1 | 3/2002 |
| EP | 1 421 913 A1 | 5/2004 |

* cited by examiner

*Primary Examiner*—Samir A. Ahmed
*Assistant Examiner*—Atiba O Fitzpatrick

(57) ABSTRACT

The present invention relates to a method for imaging using an image-generating, endoluminal instrument (1) by means of which a sequence of 2D image data of a hollow channel (2), in particular a vessel, of an object under investigation is recorded, wherein the images are recorded in a known temporal relation to a periodic movement of the object under investigation and spatial coordinates of the image are captured by means of a position sensor during each recording of an image (5) and stored as position data (9, 10) together with the 2D image data of the image (5). The method is characterized in that first position data (10) which does not lie in a predefinable movement phase of the object under investigation is corrected, before or after being stored, by interpolation between second position data (9) which does lie in the specified movement phase and/or by subtraction or addition of predetermined values. By means of the method a movement correction of the data can be performed without the need to reduce the volume of recorded image material.

8 Claims, 3 Drawing Sheets

METHOD FOR ENDOLUMINAL IMAGING WITH MOVEMENT CORRECTION

CROSS REFERENCE TO RELATED APPLICATIONS

This application claims priority to the German application No. 10 2004 011 156.1, filed Mar. 8, 2004 which is incorporated by reference herein in its entirety.

FIELD OF INVENTION

The present invention relates to a method for imaging using an image-generating, endoluminal instrument by means of which a sequence of 2D image data of a hollow channel, in particular a vessel, of an object under investigation is recorded, wherein the images are recorded in a known temporal relation to a periodic movement of the object under investigation and spatial coordinates of the image are captured by means of a position sensor during each recording of an image and stored as position data together with the 2D image data of the image.

BACKGROUND OF INVENTION

Image-generating, endoluminal instruments can be used for recording two-dimensional images of the interior of a hollow channel, in particular of a vessel or a hollow organ. Image-generating methods such as intravascular ultrasound (IVUS), optical coherence tomography (OCT) or fluorescence imaging are used in this area. The images are recorded here during the continuous or stepwise monitored movement of the instrument in the hollow channel. Thus, image-generating intravascular catheters for example can be used to produce two-dimensional cross-sectional images from the interior of vessels, from the vascular system of the heart for example. In this regard FIG. 1 shows by way of example a cross-section through a vascular system 3, with the image-generating catheter 1 introduced into one of the vessels 2 being recognizable in the figure. Said catheter 1 is advanced or retracted in the vessel either mechanically or manually by means of a movement control device 4. The pull direction of the catheter 1 is indicated by the arrow. Two-dimensional cross-sectional images of the vessel are recorded at regular intervals during the continuous, monitored movement of the catheter 1 in the vessel 2. The 2D cross-sectional images 5 obtained at different positions in the vessel 2 during the movement of the catheter 1, each of which represents a cross-section transversely to the longitudinal axis of the vessel 2, are shown on the right-hand side of FIG. 1. The arrow running along the 2D cross-sectional images 5 represents the direction in which the catheter 1 is pulled during the recording of the image. The 2D cross-sectional images show the vessel wall 7 and the central axis 8 of the vessel within the vessel lumen 6 on which the catheter 1 is guided.

DE 199 19 907 A1 discloses a method of catheter navigation in three-dimensional vascular tree images in which the spatial position of the catheter is detected and inserted into a 3D view of a preoperatively recorded vascular tree. For this purpose a catheter having an integrated position sensor is used by means of which the current spatial position of the catheter tip is detected. By registration of the position sensor with the 3D image data it is possible to display the current spatial position at any given time at the correct position in the 3D view.

The use of an image-generating endoluminal instrument, a catheter or endoscope for example, having a position sensor enables the three-dimensional reconstruction of the anatomy mapped by means of the catheter from the recorded sequence of 2D image data. The position sensing during the image recording also permits the assignment to intraoperative 2D X-ray fluoroscopy images, with the aid of which the user has points of reference when guiding the catheter. It is furthermore possible on account of the knowledge of the respective spatial position during the recording of each image to register or fuse the recorded 2D image data in a simplified manner with 3D image data obtained either preoperatively, by means of computer tomography or magnetic resonance tomography for example, or intraoperatively, by means of 3D rotation angiography or 3D ultrasound for example.

SUMMARY OF INVENTION

However, with the last-mentioned techniques for further processing of the recorded data, assignment problems which lead to errors or artifacts in the image representation occur due to movements of the patient during the recording of the images, in particular as a result of respiration or heartbeat. Consequently a 3D reconstruction based on the position data is rendered inaccurate due to the patient's breathing and therefore results in artifacts in the reconstructed 3D volume, since the respiratory activity of the patient leads to undesirable movements of the position sensor. The same problems arise in particular with intravascular image recordings due to the patient's heartbeat, which likewise leads to undesirable movements of the position sensor during the recording of the images.

These problems apply in the same way during the assignment of the catheter images to 2D X-ray fluoroscopy images, which assignment is performed incorrectly due to the movements of the position sensor. This can result in the catheter tip being represented at the wrong position in the 2D X-ray fluoroscopy image.

3D image data recorded preoperatively or intraoperatively by means of a 3D imaging procedure is usually obtained or reconstructed at a defined instant in the cardiac cycle. In this case, too, a registration or fusing of the recorded 2D image data with this 3D image data leads to errors if the 2D image data was not recorded in the same cardiac cycle as the 3D image data.

Previously these problems have been solved on the one hand by means of what is referred to as ECG or breath gating, in which the 2D image data was recorded only during a predetermined phase of the movement cycle in each case. In the case of a further comparable technique, although the images are obtained independently of the movement phase, only the 2D image data recorded in the predetermined movement phase is taken into account during the further processing. This leads to a very considerable reduction in the number of usable two-dimensional images.

An object of the present invention is to specify a method for imaging using an image-generating endoluminal instrument by means of which errors or artifacts due to a periodic movement of the area under investigation are avoided or reduced during the further processing of the recorded image data without limiting the number of usable images.

This object is achieved by the claims. Advantageous embodiments of the method are the subject matter of the dependent claims or can be derived from the following description and the exemplary embodiments.

In the present method for imaging using an image-generating endoluminal instrument by means of which a sequence of 2D image data of a hollow channel, in particular a vessel, of an object under investigation is recorded, the images are recorded in a known temporal relation to a periodic movement of the object under investigation, with spatial coordinates of the instrument being captured by means of a position sensor during each recording of an image and stored as position data together with the 2D image data of the image. The method is characterized in that first position data which does not lie in a predefinable movement phase of the object under investigation is corrected, before or after being stored, by interpolation between second position data which lies in the specified movement phase and/or by subtraction or addition of predetermined values.

With the present method, therefore, all position data of the position sensor that is captured during the recording of a 2D image and was not captured in relation to a defined movement phase, for example an ECG or breath gating phase, is modified such that the effects due to the movement are minimized. Different techniques which can be used for correcting the first position data according to the present method will be explained briefly below and in more detail in the exemplary embodiments. The embodiments relate here to the two periodic movements typically occurring during the imaging performed on a patient, namely the respiratory movement and the movement due to cardiac activity.

In one embodiment of the present method in which the first position data is corrected by subtraction or addition of predetermined values, these values are determined by the recording of a movement curve at at least one position of the instrument by means of the position sensor inside the hollow channel. In this case the instrument is fixed in the hollow channel and the sensor positions are recorded during one or more movement cycles. The resulting movement curve, which contains the position data as a function of time or of the movement phase, is stored. In the recording of the position data over a plurality of movement cycles the result can be improved by averaging over these cycles. During the correction of the first position data the corresponding value in the stored movement curve of the same movement phase is now subtracted from or added to the first position data in each case. In this way a movement correction of the first position data is performed, with the result that during the further processing of the image data, in which the position data plays a significant role, errors caused by the periodic movement are minimized.

The values subtracted from or added to the first position data also correspond to spatial coordinates as a result of the recording of these values. In this case, depending on the application, said values can be location-independent, so that only a single movement curve is recorded. In a development of the present method, however, a plurality of such movement curves are recorded at different positions of the instrument inside the hollow channel. The correction of the first position data is then performed not only as a function of the movement phase during which it was recorded, but also as a function of the spatial position. At the same time values to be added or subtracted at positions at which no movement curve was recorded are interpolated between the respective adjacent movement curves or their values. In this case a linear interpolation or even a higher-order interpolation method can be performed.

Depending on the application, the correction of the position data can be performed either already immediately after the capture of said position data or only after the acquisition of all the image material. The movement curves are preferably recorded before the image acquisition is performed. During the recording of a plurality of movement curves at different positions in particular it is, however, also possible to generate these movement curves during the acquisition of the image data at the different positions.

In a further embodiment of the present method the first position data is replaced by interpolated position data, without the need to record movement curves for this purpose. The interpolation, a linear interpolation or a higher-order interpolation, is performed in this case between the respective adjacent second position data which is assigned to the specified movement phase. Thus, the actual position information of the position sensor is only considered at a defined relevant instant in the movement phase. The other position information is interpolated between these base points. This technique likewise leads to a reduction in errors or artifacts during the further processing of the recorded 2D image data.

A combination of the aforementioned techniques, for different areas of the investigated hollow channel for example, or an extension for correction of both respiration- and heartbeat-induced errors is useful depending on application and investigation conditions.

With the present method for reducing or eliminating a periodic movement, in particular a respiration- and/or heartbeat-induced movement, of the position sensor, errors or movement artifacts are reduced or avoided during the further processing of the recorded image data. A 3D reconstruction from the recorded 2D image data is therefore possible without reconstruction artifacts caused by the patient's breathing or heartbeat and without a reduction in the number of recorded images. After selection of a defined instant in the movement cycle the 3D reconstruction can be performed at precisely this instant. By means of this retrospective gating a 4D representation of the 2D images is also possible by performing the 3D reconstruction in relation to successive instants in a movement cycle. The precision of the assignment of 2D X-ray fluoroscopy images to the 2D images of the endoluminal instrument is also increased, since the undesirable effects of the patient's breathing and heartbeat on the assignment of the images are reduced or eliminated.

A 3D volume of the recorded 2D image data reconstructed at a defined instant in the movement cycle can be precisely registered or fused with anatomical 3D image data, obtained for example from computer tomography, magnetic resonance tomography, 3D rotation angiography or a 3D ultrasound recording, which image data was recorded at the same defined instant in the movement cycle. Equally possible is the 4D-4D fusion of reconstructed image sequences of the image data recorded with the endoluminal instrument with sequences of reconstructed anatomical 3D image data of the above-mentioned 3D image-generating procedures.

As a result of the correction of the position data being performed by means of the present method any movement phase of the movement cycle can be specified at which the reconstruction of the image data can then be performed. This allows a greater degree of freedom in the further processing of the image data, without reducing the volume of the recorded image material.

In order to perform the method an arrangement having an image-generating endoluminal instrument with position sensor is required in which there is provided in the assigned computer unit for controlling the instrument and recording the image data a module which performs the correction of the first position data in accordance with the present method. In the case of a subtraction or addition of predetermined values the one or more associated movement curves are stored in said computer unit.

BRIEF DESCRIPTION OF THE DRAWINGS

The present method will be explained again in more detail below with reference to exemplary embodiments in connection with the drawings, in which.

Figure 1:
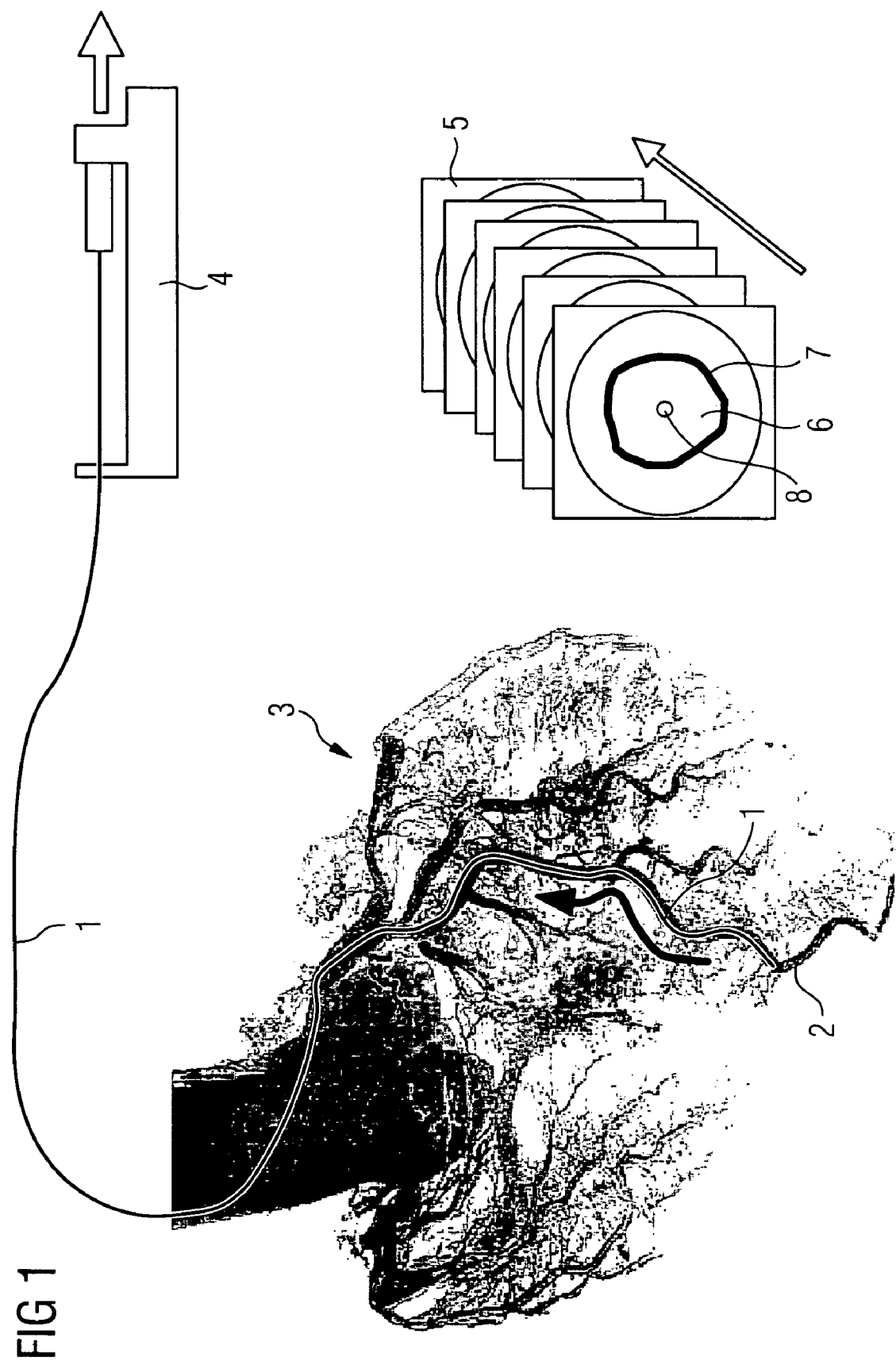
FIG. 1 is a representation of the conditions during the recording of 2D cross-sectional images by means of a catheter.
Figure 2:
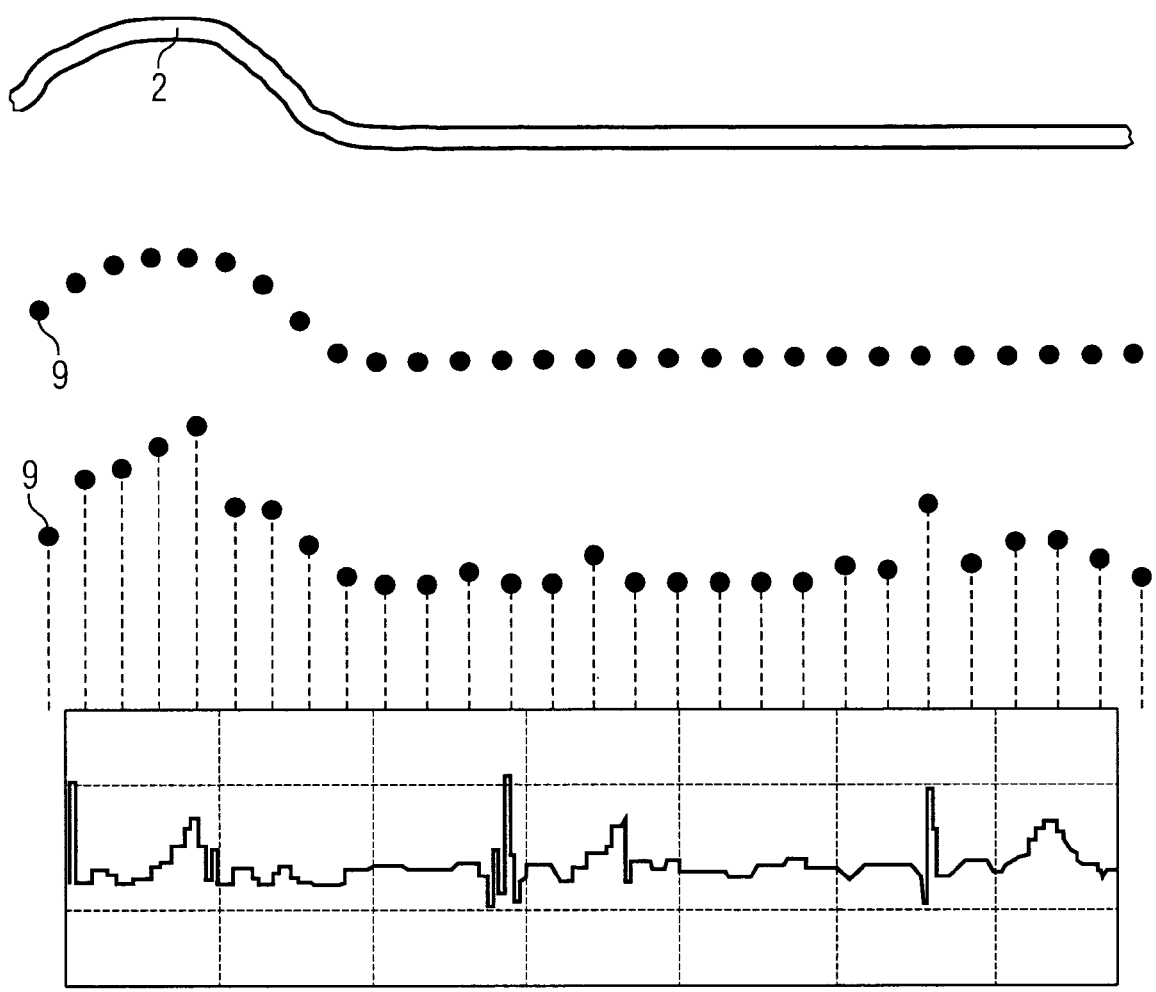
FIG. 2 shows an example of the effect of the cardiac movement on the position data captured during the recording of the images.

The conditions during the recording of 2D image data within a vessel have already been explained in the introduction to the description in connection with FIG. 1. When a catheter 1 having a position sensor is used, 5 spatial coordinates are supplied as position data associated with the recording of each 2D image, the coordinates reflecting the exact position of the image recording of each 2D image. On the basis of this position data a 3D volume can be reconstructed from the 2D image data or this image data can be registered with other 2D or 3D image data. However, during the recording of this position data problems arise due to unavoidable movements of the vessel which are caused by the patient's heartbeat and possibly also breathing. These problems are illustrated with the aid of FIG. 2. In the top image in this figure can be seen by way of example an actual course of the vessel 2 through which the catheter 1 is guided. During the image recording within this vessel 2 the position data 9 supplied by the position sensor should ideally yield the course shown in the center part of FIG. 2.

Due to the heartbeat, however, the spatial coordinates actually supplied by the position sensor produce a distorted course, as represented in the lower part of the figure. In this lower part the patient's heartbeat can be seen in the ECG, the heartbeat having an effect on the current position of the vessel and consequently on the position data 9 supplied by the position sensor, as indicated schematically in the lower part. Further processing of the acquired image data on the basis of this position data which has been distorted by the movement of the heart would therefore lead to error or image artifacts in the subsequent representation of the image.

In order to reduce or eliminate this heartbeat-induced movement of the position sensor, three variants are proposed in the present example. In the first variant the catheter is initially fixed in a vessel. In a learning phase the sensor positions are recorded during a cardiac cycle and stored as a movement curve. It is of course also possible to average over a plurality of cardiac cycles in order to obtain the movement curve. At the start of the image recording the movement curve is correlated with the patient's actual heartbeat. This can be accomplished using known ECG techniques. During catheter guidance and the acquisition of the catheter images the corresponding value of the movement curve is then subtracted for each captured sensor position.

Figure 3:
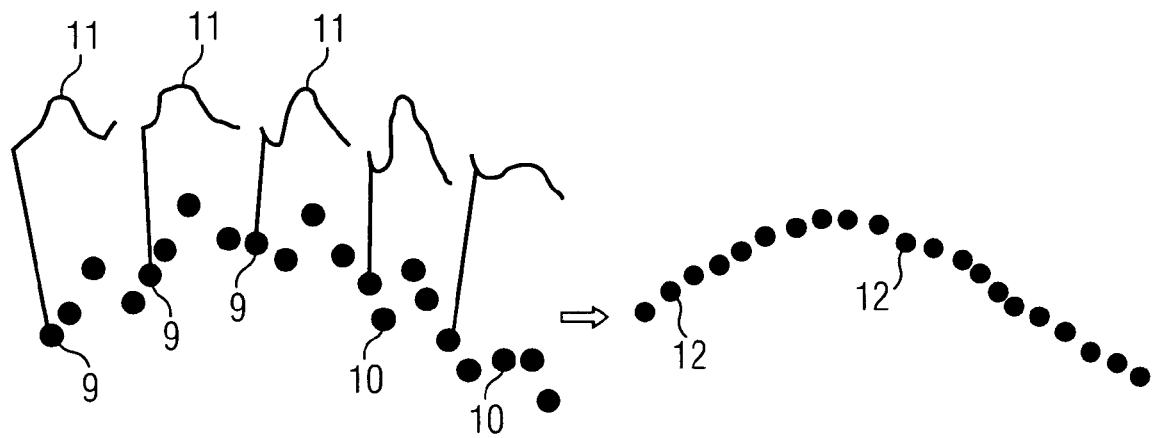
FIG. 3 shows an example of a correction of the position data according to an embodiment of the present method.

In a further variant, in contrast to the preceding first variant, a location-dependent heartbeat-induced movement is assumed, so that different heartbeat-induced movements of the sensor are produced as a function of the catheter position. This location-dependent movement is compensated by fixing the catheter in more than one position and recording movement curves for each of these fixed positions. As in the preceding variant, the value to be subtracted then results from location-dependent interpolation between the recorded location-dependent movement curves. This is illustrated with the aid of FIG. 3, on the left side of which the positions 9 of the sensor captured during the image recording are shown as black dots, which positions are associated with a catheter image that was recorded at a defined instant in the cardiac cycle, synchronized with the movement curves. The further positions 10 of the sensor shown in this left side of the figure are associated with catheter images that were recorded at other, arbitrary instants in the cardiac cycle. Due to the patient's heartbeat these positions are imprecise in respect of the actual course of the vessel. By means of a correction of the inaccurate positions 10 of the sensor on the basis of the predetermined location-dependent movement curves 11, the assignment of which can also be seen on the left side of the figure, these inaccuracies in the recorded position can be eliminated or at least significantly reduced. The result can be seen on the right side of FIG. 3, where the corresponding value of the assigned movement curve 11 has been subtracted in each case from the inaccurate first position data 10 of the sensor. The positions 12 corrected in this way essentially reflect the course of the vessel, with the result that further processing of the image data using these assigned corrected positions 12 avoids errors in the reconstruction or registration of the image data.

It is also possible to generate the at least two movement curves in two fixed positions, not prior to the image recording, but during the advancement of the catheter, while the acquisition of the catheter images is performed during a possibly automatic, motorized retraction of the catheter.

Figure 4:
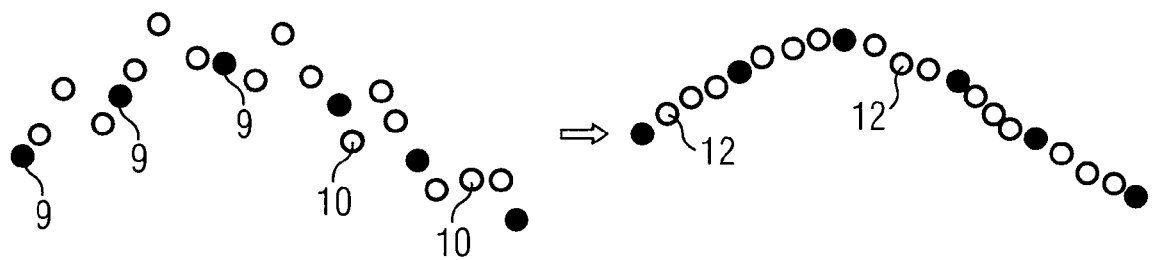
FIG. 4 shows an example of a correction of the position data according to a further embodiment of the present method.

The third variant for correcting the position data is illustrated with the aid of FIG. 4. In this case, in contrast to the preceding first and second variant, the position of the sensor is interpolated, either linearly or by means of higher-order interpolation methods, for all catheter images occurring within a cardiac cycle. Thus, the actual position information of the sensor is considered only at a defined, relevant instant in the cardiac cycles. Other position information not associated with catheter images captured at this defined instant are discarded and interpolated between the remaining base points. In this way heartbeat-induced sensor or catheter movements are eliminated. The sensor or catheter movement between two cardiac cycles is approximated by the interpolation as a constant movement in time (with linear interpolation) or as a movement curve known over time (with higher-order interpolation). What is important here is that while a sensor position is captured during the catheter guidance for each acquisition of a catheter image, only those sensor positions are subsequently used for further processing of the images that were acquired at the defined, relevant instant in the cardiac cycles. In this way retrospective gating of the catheter images is made possible.

In this regard, the left side of FIG. 4 shows on the one hand positions 9 of the sensor which are associated with a catheter image recorded at a defined instant of the cardiac cycle. On the other hand, the empty dots show positions 10 of the sensor which are associated with catheter images recorded at other, arbitrary instants in the cardiac cycle. Due to the patient's heartbeat these positions 10 are inaccurate in respect of the actual course of the vessel and are replaced by interpolated position data 12. The interpolation takes place here between the respective adjacent positions 9 which are associated with the defined cardiac cycle and serve as base points for the interpolation. On the right side of the figure can be seen the position data 12 obtained by this interpolation, which data in combination with the established position data 9 reflects the actual course of the vessel with good correspondence. This interpolation method lends itself in particular to use with slow catheter guidance, since then the interpolation yields the most accurate values.

The aforementioned variants can, of course, also be used for the correction of respiration-induced movement, in which case the synchronization can then be accomplished for example by deep inhalation at the beginning of the image recording.

The invention claimed is:

1. A method of creating a medical image using an endoluminal imaging device, comprising:
   recording with a computer a sequence of two-dimensional images of a hollow cardio duct by the endoluminal imaging device during a periodical movement having predictable and unpredictable cardio movement phases of a subject to be examined, the hollow duct belonging to the subject to be examined, wherein the hollow duct is a vessel and the periodical movement having predictable and unpredictable cardio movement phases comprises a sequence of heartbeats of the subject;
   determining current spatial coordinates of the endoluminal imaging device when recording each of the two-dimensional images by a position detecting sensor disposed in the endoluminal imaging device;
   storing in a memory of the computer a plurality of position datasets each including the current spatial coordinates from the position detecting sensor disposed in the endoluminal imaging device and the related two-dimensional image;
   correcting with a correction module of the computer a first of the position datasets corresponding to a non predictable cardio movement phase based on a second of the position datasets corresponding to a predictable cardio movement phase, wherein the correcting comprises discarding each of the position datasets corresponding to the non predictable cardio movement phase and replacing the discarded position datasets with position datasets interpolated between adjacent position datasets corresponding to the predictable cardio movement phase; and
   using the corrected position dataset to construct a volumetric three-dimensional image of the cardio duct,
   wherein the position detecting sensor is a sensor that determines a current spatial position of the endoluminal imaging device.

2. A method of creating a medical image using an endoluminal imaging device, comprising:
   recording with a computer a sequence of two-dimensional images of a hollow cardio duct by the endoluminal imaging device during a periodical movement having predictable and unpredictable cardio movement phases of a subject to be examined, the hollow duct belonging to the subject to be examined, wherein the hollow duct is a vessel and the periodical movement having predictable and unpredictable cardio movement phases comprises a sequence of heartbeats of the subject;
   determining current spatial coordinates of the endoluminal imaging device when recording each of the two-dimensional images by a position detecting sensor disposed in the endoluminal imaging device;
   during a learning phase, while the endoluminal imaging device is at one location in a vessel of the subject affected by the sequence of heartbeats, recording a plurality of sensor positions with the position detecting sensor disposed in the endoluminal imaging device to obtain a movement graph indicative of a position perturbation occurring at the one location in the vessel due to the sequence of heartbeats;
   storing in a memory of the computer a plurality of position datasets each including the current spatial coordinates from the position detecting sensor disposed in the endoluminal imaging device and the related two-dimensional image;
   correcting with a correction module of the computer a first of the position datasets corresponding to a non predictable cardio movement phase by adding or subtracting correcting values obtained from the movement graph to the corresponding image data values included in the first position dataset; and
   using the corrected position dataset to construct a volumetric three-dimensional image of the cardio duct,
   wherein the position detecting sensor is a sensor that determines a current spatial position of the endoluminal imaging device.

3. The method according to claim 1, wherein the subject to be examined is a patient.

4. The method according to claim 2, wherein the subject to be examined is a patient.

5. The method according to claim 2, wherein the movement graph is recorded before the recording the sequence of two-dimensional images.

6. A method of creating a medical image using an endoluminal imaging device, comprising:
   recording with a computer a sequence of two-dimensional images of a hollow cardio duct by the endoluminal imaging device during a periodical movement having predictable and unpredictable cardio movement phases of a subject to be examined, the hollow duct belonging to the subject to be examined, wherein the hollow duct is a vessel and the periodical movement having predictable and unpredictable cardio movement phases comprises a sequence of heartbeats of the subject;
   determining current spatial coordinates of the endoluminal imaging device when recording each of the two-dimensional images by a position detecting sensor disposed in the endoluminal imaging device;
   as the endoluminal imaging device travels in a vessel of the subject affected by the sequence of heartbeats, at multiple locations in the vessel, recording a plurality of sensor positions with the position detecting sensor disposed in the endoluminal imaging device to obtain a location-dependent movement graph for each of said multiple locations, each respective one of the location-dependent movement graphs indicative of a position perturbation occurring at a respective one of the multiple locations in the vessel due to the sequence of heartbeats;
   storing in a memory of the computer a plurality of position datasets each including the current spatial coordinates from the position detecting sensor disposed in the endoluminal imaging device and the related two-dimensional image;
   correcting with a correction module of the computer a first of the position datasets corresponding to a non predictable cardio movement phase by adding or subtracting correcting values obtained from respective ones of the location-dependent movement graphs to the corresponding image data values included in the first position dataset; and
   using the corrected position dataset to construct a volumetric three-dimensional image of the cardio duct, wherein the position detecting sensor is a sensor that determines a current spatial position of the endoluminal imaging device.

7. The method according to claim 6, wherein a further movement graph is determined by interpolating between two of the movement graphs related to adjacent locations, the further movement graph corresponding to a location located between the adjacent locations.

8. The method as claimed in claim 6, wherein the movement graph is recorded in parallel with recording the sequence of two-dimensional images.

* * * * *

UNITED STATES PATENT AND TRADEMARK OFFICE
CERTIFICATE OF CORRECTION

| | | |
|---|---|---|
| PATENT NO. | : 7,657,069 B2 | Page 1 of 1 |
| APPLICATION NO. | : 11/076537 | |
| DATED | : February 2, 2010 | |
| INVENTOR(S) | : Boese et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 982 days.

Signed and Sealed this

Thirtieth Day of November, 2010

David J. Kappos
*Director of the United States Patent and Trademark Office*